(12) United States Patent
Cully et al.

(10) Patent No.: US 8,781,601 B2
(45) Date of Patent: Jul. 15, 2014

(54) ATRAUMATIC LEAD REMOVAL SHEATH

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Aaron J. Hopkinson, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/692,409

(22) Filed: Dec. 3, 2012

(65) Prior Publication Data
US 2013/0096663 A1    Apr. 18, 2013

Related U.S. Application Data

(62) Division of application No. 12/397,886, filed on Mar. 4, 2009, now Pat. No. 8,326,437.

(51) Int. Cl.
*A61N 1/05*    (2006.01)

(52) U.S. Cl.
USPC .......................................................... 607/116

(58) Field of Classification Search
USPC .................................. 604/7–8, 21; 623/1.12
See application file for complete search history.

(56) References Cited

U.S. PATENT DOCUMENTS

| | | | |
|---|---|---|---|
| 3,583,391 A | 6/1971 | Cox et al. | |
| 4,883,070 A | 11/1989 | Hanson | |
| 5,112,309 A | 5/1992 | Bertaud et al. | |
| 5,609,622 A | 3/1997 | Soukup et al. | |
| 5,755,762 A | 5/1998 | Bush | |
| 5,779,670 A | 7/1998 | Bidwell et al. | |
| 5,807,399 A | 9/1998 | Laske et al. | |
| 5,824,041 A | 10/1998 | Lenker et al. | |
| 5,846,251 A | 12/1998 | Hart | |
| 5,902,329 A * | 5/1999 | Hoffmann et al. | 607/121 |
| 6,007,488 A * | 12/1999 | Jaker et al. | 600/300 |
| 6,122,552 A | 9/2000 | Tockman et al. | |
| 6,704,604 B2 | 3/2004 | Soukup et al. | |
| 7,020,529 B2 | 3/2006 | Krall et al. | |
| 7,367,975 B2 * | 5/2008 | Malecki et al. | 606/41 |
| 7,425,202 B2 * | 9/2008 | Huang et al. | 600/564 |

(Continued)

OTHER PUBLICATIONS

Zoll CZ, Bauer O, Al Hasani S, et al. Transcervical Intrauterine Embryo Transfer (ET) with a New Everting Catheter and "Peel-Back" Technique1. Journal of Assisted Reproduction and Genetics 1996;vol. 13 No. 5: 452-455.

(Continued)

*Primary Examiner* — Carl H Layno
*Assistant Examiner* — Paula J Stice
(74) *Attorney, Agent, or Firm* — Paul J. Fordenbacher, Esq.

(57) ABSTRACT

The present invention provides for a safer and less traumatic chronically implanted device and methods for removing same from a patient. One embodiment of the invention provides for a medical device comprising an implantable diagnostic or therapeutic lead having a distal end, a proximal end, a longitudinal axis and an outer surface, and a tubular cover attached to the diagnostic or therapeutic lead, preferably near the distal end, and positioned to cover a substantial portion of the outer surface of the diagnostic or therapeutic lead. The tubular cover is configured to evert upon application of a longitudinal force to extract the diagnostic or therapeutic lead.

32 Claims, 9 Drawing Sheets

(56) References Cited

U.S. PATENT DOCUMENTS

| | | |
|---|---|---|
| 2001/0044595 A1 | 11/2001 | Reydel et al. |
| 2002/0095100 A1* | 7/2002 | Lee et al. ............... 600/564 |
| 2002/0147486 A1 | 10/2002 | Soukup et al. |
| 2003/0023294 A1 | 1/2003 | Krall et al. |
| 2005/0004642 A1 | 1/2005 | Shoberg |
| 2005/0197595 A1 | 9/2005 | Huang et al. |
| 2006/0015135 A1 | 1/2006 | Vrba et al. |
| 2006/0106442 A1 | 5/2006 | Richardson et al. |
| 2006/0282144 A1* | 12/2006 | Knapp et al. ............. 607/116 |
| 2007/0169877 A1 | 7/2007 | Leeflang et al. |
| 2007/0198077 A1 | 8/2007 | Cully et al. |
| 2007/0224243 A1 | 9/2007 | Bayston |
| 2009/0182411 A1 | 7/2009 | Irwin et al. |

OTHER PUBLICATIONS

Love et al. Recommendations for Extraction of Chronically Implanted Transvenous Pacing and Difibrillator Leads: Indications, Facilities, Training. PACE 2000 23:544-551.

Ellenbogen KA et al. Clinical Cardiac Pacing, Defibrillation, and Resynchronization Therapy (Philadelphia, PA. Saunders Elsevier, 2007), 885- 886.

* cited by examiner

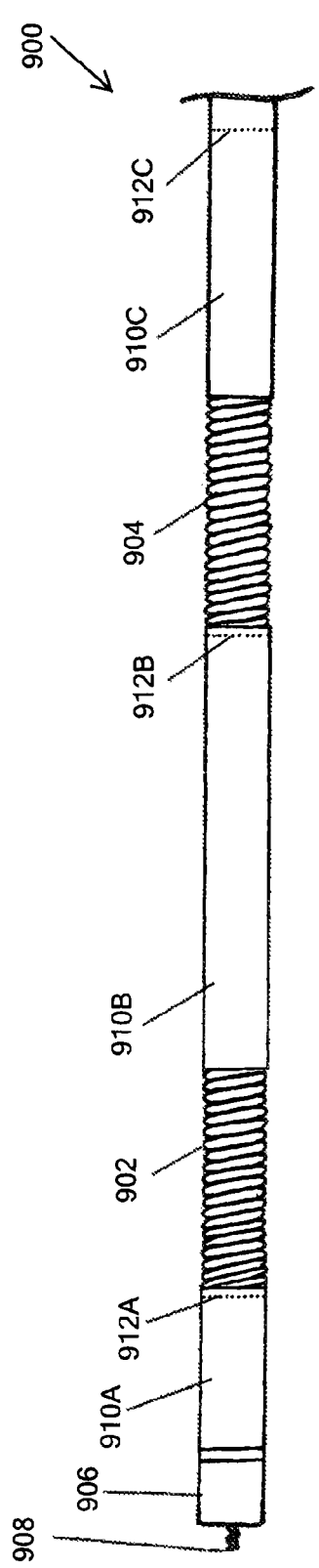
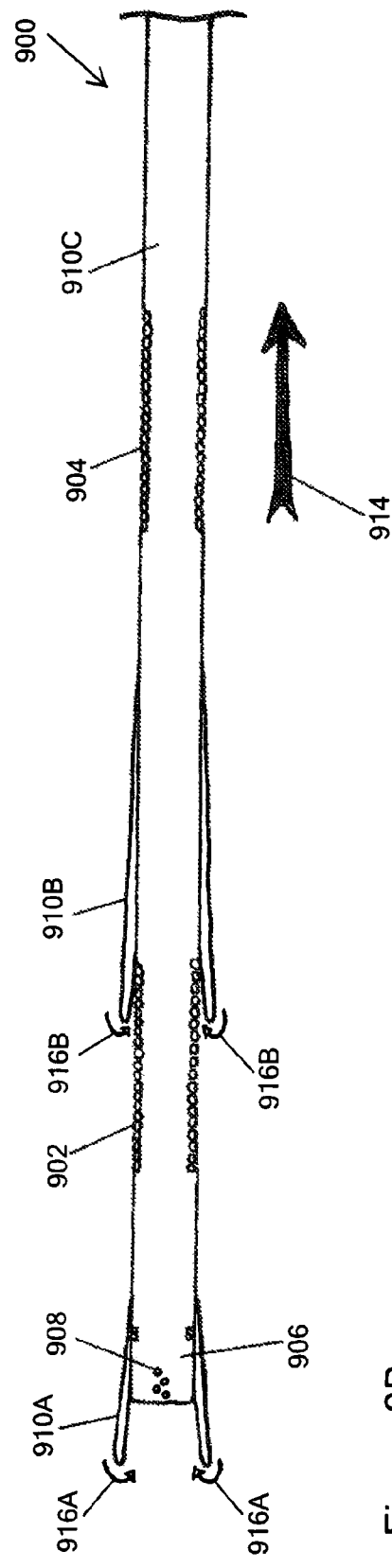
Figure 9A
Figure 9B

ATRAUMATIC LEAD REMOVAL SHEATH

CROSS REFERENCE TO RELATED APPLICATIONS

This application is a divisional of U.S. application Ser. No. 12/397,886 filed Mar. 4, 2009 now U.S. Pat. No. 8,326,437.

FIELD OF THE INVENTION

The present invention relates to atraumatic removal of chronically implanted medical devices.

BACKGROUND OF THE INVENTION

It is sometimes necessary to extract chronically implanted medical devices, particularly endocardial leads for use with pacemakers and implantable cardioverter-defibrillators (ICDs), if such leads fail or should infection develop.

Removal of such implanted devices presents several obstacles. For example, fibrous tissue growth along any portion of a cardiac lead may hamper extraction and can lead to trauma in adjacent cardiovascular tissues.

Various methods have been developed to remove chronically implanted devices. For cardiac leads, a common removal method is traction, wherein a longitudinal force is applied to the lead body after exteriorizing the proximal end of the lead. However, complications and difficulties encountered when using traction have prompted development of surgical approaches and intravascular counterpressure and countertraction (Love et al. PACE 2000 23:544-551).

Surgical approaches involve exposing the heart and great veins via sternotomy or thoracotomy followed by extraction of the lead via a transmural incision in the atrium or ventricle. While this removal technique is generally successful, it requires skills not generally available and is associated with morbidity and high cost (Love et al. PACE 2000 23:544-551).

In cardiovascular countertraction, a sheath made of polymer or metal slides distally over the lead body. A locking stylet may be passed through the interior of the lead and locked at the lead tip to localize traction forces at the tip. Traction applied to the lead pulls ingrown tissue to the sheath. Traction force is countered by the tip circumference of the sheath which applies a localized shear stress on the fibrotic tissue, separating it from the lead body. (Ellenbogen, Kenneth A., and others, ed. Clinical Cardiac Pacing, Defibrillation, and Resynchronization Therapy (Philadelphia, Pa. Saunders Elsevier, 2007), 885-886.)

Counterpressure is a similar extraction technique used when calcified tissues are present in which countertraction force is converted to pressure localized between the edge of the sheath and adjacent tissues. This pressure peels calcified masses from the vein and/or heart walls, thus damaging the tissues (Ellenbogen, 2007, 886).

Alternative sheaths include those using powered, mechanical cutting tips, RF ablation and laser vaporization. (Ellenbogen, 2007, 886-890.) However, each method is associated with significant risks. Therefore there is a need for an alternative and safer method of extracting medical devices from a patient.

SUMMARY OF THE INVENTION

The present invention provides for a safer and less traumatic device and methods for removing a chronically implanted device in a patient. One embodiment of the invention provides for a medical device comprising an implantable diagnostic or therapeutic lead having a distal end, a proximal end, a longitudinal axis and an outer surface; and a tubular cover attached to the diagnostic or therapeutic lead, preferably near the distal end, and positioned to cover a substantial portion of the outer surface of the diagnostic or therapeutic lead. The tubular cover is configured to evert upon application of a longitudinal force to extract the diagnostic or therapeutic lead.

The present invention also provides for an evertable tubular cover surrounding portions of a lead, whereby portions of said lead will not be covered. In another embodiment, a lead will be comprised of several types of tubular covers, wherein said covers are evertable when the lead is extracted following implantation. In another embodiment, said tubular cover will tear and evert from specific sections where there is tissue attachment, tissue ingrowth or another type of constraint that causes said tubular cover to tear as a lead is extracted. In another embodiment, said tear away tubular cover comprises a means of permitting tearing in specific locations along the longitudinal axis of said tubular cover. In one embodiment, said means comprise perforations being generally oriented circumferentially around the tubular cover. In another embodiment, said perforations are oriented in helical pattern around the tubular cover. In another embodiment, said means comprise weakened areas of material that will tear circumferentially and evert as a lead is extracted.

The present invention also provides a tubular cover for attachment to a diagnostic or therapeutic lead configured to allow energy to pass from the lead and into adjacent fluids or tissue. Alternatively, the lead may be configured to allow energy to pass from adjacent fluids or tissue into the lead, for example in the case of sensing by cardiac pacing leads. The tubular cover may be attached to at least the distal end of the lead and positioned to cover a substantial portion of the outer surface of the lead. The tubular cover is configured to evert upon application of a longitudinal force to extract the lead. Where the lead conducts electrical energy into adjacent fluids or tissues, the tubular cover allows both such energy transfer and gases generated by electrolysis to pass into adjacent fluids. This avoids damage to the lead or the cover. Where energy is conducted from surrounding fluids and tissues into the lead, the tubular cover also allows such transfer.

The present invention also provides for a medical device comprising a tubular cover, said tubular cover configured to evert upon application of a longitudinal force to the medical device following implantation. In one embodiment, said medical device is chronically implanted in an animal. In another embodiment, said medical device is prone to tissue incorporation. In another embodiment, said tubular cover comprises ePTFE. In another embodiment, wherein said medical device is selected from the group consisting of lead generators, arteriovenous (A-V) access catheters, peripherally inserted central (PICC) catheter lines, venous feeding catheters, feeding tubes, breathing tubes, and implanted sensing devices.

The present invention also provides methods for making and extraction of diagnostic or therapeutic leads with tubular covers of the invention with minimal damage to surrounding tissues.

DESCRIPTION OF THE DRAWINGS

FIGS. 9A and 9B depict an alternative embodiment of the tubular cover of the invention.

DETAILED DESCRIPTION OF THE INVENTION

Figure 1:
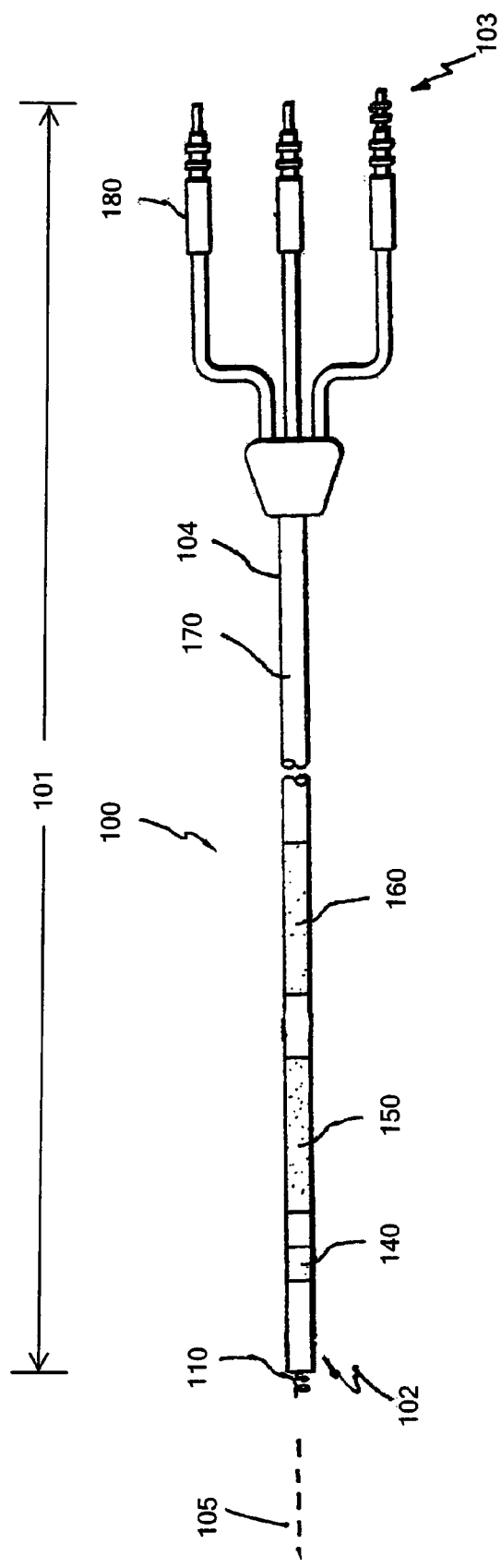
FIG. 1 shows a typical cardiac pacing and ICD lead.

While the present invention will hereinafter be described in connection with the preferred embodiments and methods of use thereof, it will be understood that it is not intended to limit the invention to these embodiments and methods of use. Instead, it is intended to cover all alternatives, modifications, and equivalents as may be included within the spirit and scope of the invention as described and claimed.

The present invention solves a long felt need in the medical field, providing an implantable medical device which can be removed after implant without causing significant risk or complications, including trauma to the tissue in which said medical device was implanted or to the surrounding tissue. This need is especially pronounced for diagnostic or therapeutic leads.

In one embodiment, the medical device comprises a diagnostic or therapeutic implantable transmission lead with an evertable tubular cover surrounding at least a portion the lead. The term "implantable transmission lead" is meant to include an implantable lead construct having a length, a distal end, a proximal end, an outer surface and a longitudinal axis, wherein said lead is capable of delivering energy to or from the body or bodily fluids, typically in the form of electrical energy, but may also include acoustic energy and electromagnetic energy, such as light. Such energy may be beneficial for a range of medical applications such as cardiac pacing and defibrillation, neurological sensing and stimulation, physiological sensing, diagnostic applications, therapeutic applications, signal transmission applications, or other similar functions a device implanted in a subject may deliver to or receive from the body.

Alternatively, the device comprises an implantable transmission lead with an evertable tubular cover surrounding at least a portion of the lead. In one embodiment, the cover is capable of allowing energy to pass through the tubular cover (from the lead and into adjacent fluids or tissue). In another embodiment, said energy is electrical energy. In another embodiment, said tubular cover allows gases generated by electrolysis to pass through the cover and into adjacent fluids. For example, a typical defibrillation electrode out-gasses and forms undesirable bubbles during rapid, repeated energy pulses. Bubble formation at an electrode is described by G H Bardy et al. Circulation 73, 525 538, March 1986. The formation of bubbles at the electrode degrades the energy waveform. Excessive bubble formation can result in increased conduction resistance, which raises the energy required for defibrillation and increases local current density. Thus, for a lead which transmits electrical energy, it would be desirable to have gas and/or bubbles (comprised of said gas) to diffuse through the tubular cover.

By "implantable" it is meant that the device is suited for embedding into a body of an animal, e.g. a human, surgically (i.e. via an incision) or other methods known in the art. In one embodiment, an implantable lead is chronically implanted in an animal. "Chronically implanted" is considered to include, but is not limited to, long term implantation (e.g. at least 29 days) and/or at least a period of time sufficient to generate tissue growth into (tissue ingrowth/incorporation) and/or tissue adhesion by tissue growth onto (tissue attachment/adhesion) an implanted medical device.

By "evert", "evertable", "everted" it is meant that the tubular cover folds onto itself such that an outer surface becomes an inner surface, or conversely an inner surface becomes an outer surface. See, for example, FIGS. 6A and B.

Referring to the drawings in which like reference numbers represent like or corresponding elements in the drawings.

FIG. 1 illustrates an implantable lead 100 of the conventional bipolar pacing and ICD type. The implantable lead 100 has a length 101, a distal end 102, a proximal end 103, an outer surface 104 and a longitudinal axis 105 which are coaxial with the implantable lead. The lead has one or more proximal connectors 180 for connecting to a power source and operating system (not shown). A lead body 170 extends toward the distal end 102. Two electrodes 150 and 160 serve as needed to defibrillate the heart. The pacing and sensing circuit is formed by pacing electrode 110 which, in this case, is shaped as a moveable helical coil and sensing ring 140. The operating system sends electrical pulses for pacing and receives electrical cardiac signals through the pacing and sensing circuit.

Figure 2:
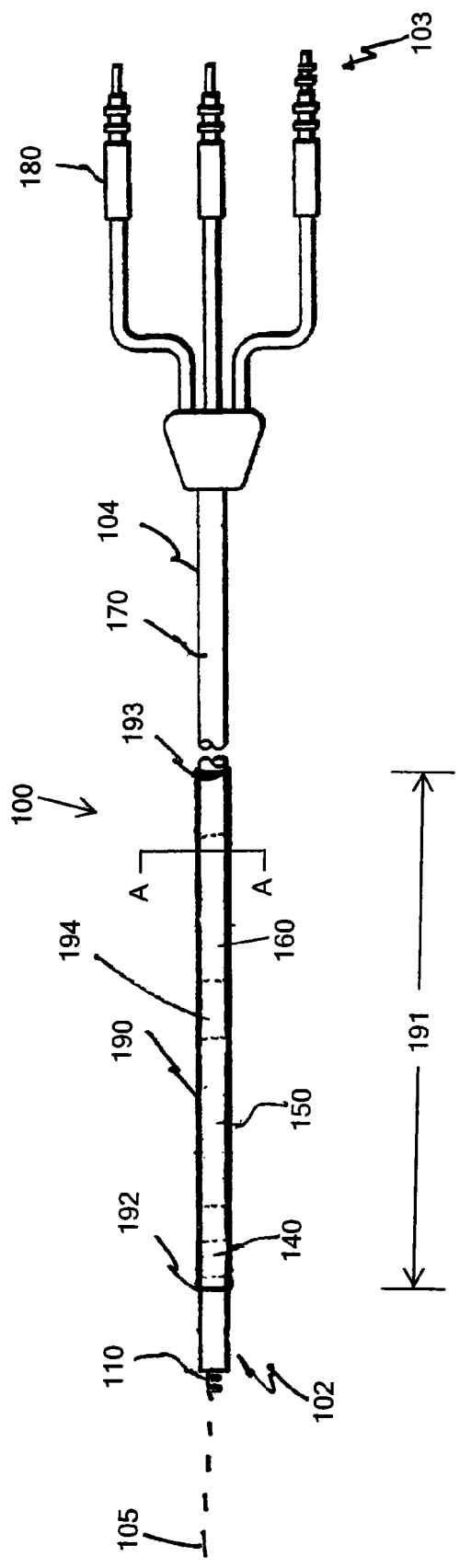
FIG. 2 shows a device of the present invention with an implantable lead and tubular cover.

FIG. 2 illustrates the implantable lead 100 and a tubular cover 190 of the present invention. The tubular cover 190 has a length 191, typically in the range of 40-100 cm, a distal end 192, a proximal end 193, an outer surface 194 and a longitudinal axis 105 centrally coaxial with the implantable lead. Typical leads have diameters of about 1.0 to about 12.0 French, or even larger, depending on intended function and implant location. The tubular cover is sized to be positioned over a substantial portion of the outer surface of the implantable lead. The term "substantial portion" refers to a covering positioned over at least about 50% of the length of the lead body 170 of said implantable lead. In another embodiment, the term "substantial portion" refers to a covering positioned over at least about 60%, about 70%, about 80%, about 90%, about 95%, about 100% of the length of the lead body 170 of said implantable lead. "Substantial portion" also includes a non-continuous covering that is positioned over a lead in segments, e.g., between electrodes or on the electrodes (140, 150, 160), thereby leaving a portion of lead body lead uncovered. FIGS. 9A and 9B illustrate an example of a non-continuous covering of an implantable lead.

Figure 3:
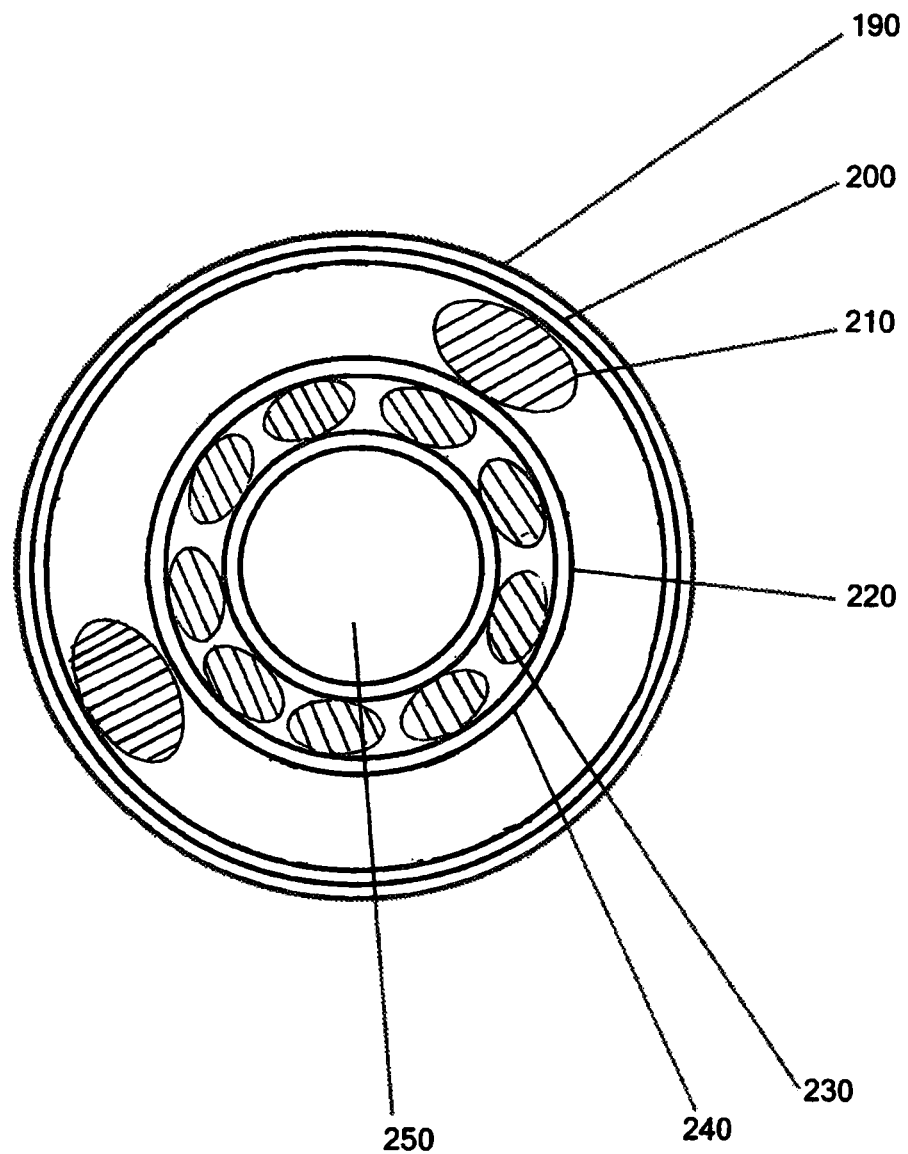
FIG. 3 is a cross section taken at A-A in FIG. 2.

FIG. 3 illustrates a cross section at "A-A" in FIG. 2. Tubular cover 190 surrounds an outer insulative layer 200 surrounding an outer coiled conductor 210. The inside of the conductor is lined with another insulative layer 220 which covers an inner coiled conductor 230. An insulative liner 240 with a lumen 250 is positioned adjacent inner conductor 230.

The tubular cover comprises a sheath-like structure that can be positioned over a substantial portion of the outer surface of an implantable lead. The tubular cover may be attached to at least the distal end of said lead by mechanical, rail or interference fit, mechanical structures, heat bonding or by a biocompatible adhesive or other securing means. Example adhesives are thermoplastic fluoropolymers, such as fluorinated ethylene propylene (FEP). The tubular cover may also be formed as an integral part of the implantable lead at manufacture, thereby not requiring any attachment. The tubular cover may also be attached to an implantable device following its manufacture as a separate component. In one embodiment, the tubular cover has "double walled" construction wherein the cover is folded back on itself. Thus, when a lead comprising an evertable "double walled" tubular cover is extracted, the cover will slide over itself, thus reducing the force necessary to extract the lead.

In another embodiment, said tubular cover will tear at specific sections where there is tissue attachment, tissue ingrowth or another type of constraint that causes said tubular cover to tear as a lead is extracted. Said tear away tubular cover comprises a means of permitting tearing in specific locations along the longitudinal axis of said tubular cover. Said means will allow the portions of the tubular cover to tear circumferentially and evert as a lead is extracted. In one embodiment, said means comprise perforations being generally oriented circumferentially around the tubular cover. In another embodiment, said perforations are oriented in helical pattern around the tubular cover. In another embodiment, said means comprise weakened areas of material that will tear circumferentially and evert as a lead is extracted. In these embodiments, said tubular cover will be secured (as described above) to the lead at strategic locations so that if said tubular cover tears, said section will evert. In some embodiments, all the sections will tear and evert as said implantable lead is extracted. In other embodiments, only a few sections will tear and evert as said implantable lead is extracted.

FIGS. 9A and 9B depict one of the embodiments described above. FIG. 9A depicts a typical cardiac lead 900 comprising electrodes 902 and 904, distal tip housing 906, and fixation member 908. FIG. 9A further comprises tear away tubular covers 910A, 910B, and 910C which comprise perforations 912A, 912B, and 912C, respectfully. In this embodiment, said tear away tubular cover is applied in different sections of lead 900, leaving electrodes 902 and 904 exposed. However, in other embodiments, a tubular cover is applied to the whole lead.

FIG. 9B depicts a cross section of lead 900 in FIG. 9A as it is extracted from an animal, e.g. a human. As shown, fixation member 908 is retracted into tip housing 906 and an extraction force, as depicted in arrow 914, is applied to lead 900. Tubular cover 910A and 910B is torn at perforations 912A and 912B (see FIG. 9A) and everts, as indicated by arrows 916A and 916B. As the lead 900 is extracted tubular cover 910A and 910B will continue to evert until lead 900 is fully extracted and/or said tubular cover is fully everted. As described above, not all sections of said tubular cover will tear, as depicted by the intact tubular cover 910C. Note, that FIGS. 9A and 9B are only meant to demonstrate one embodiment of the invention and is not to be limiting in any way.

The tubular cover is dimensioned in diameter and length to cover the desired portion of the implantable device. In one embodiment, if said tubular cover has a "double walled" construction, then the amount of material used to make said tubular cover will be at least double the length desired to cover said implantable device because said cover is located over the lead and is folded back on itself. Preferred tubular cover thicknesses are about 0.25 mm or less, about 0.23 mm or less, about 0.20 mm or less, about 0.18 mm or less, about 0.15 mm or less, about 0.13 mm or less, about 0.10 mm or less, about 0.07 mm or less, about 0.06 mm or less, about 0.05 mm or less, about 0.04 mm or less, about 0.03 mm or less, about 0.02 mm or less, about 0.01 mm or less. Cover thickness can be determined by measurement of a transverse cross-section of a covered electrode using an optical comparator, or other suitable means. The tubular cover is configured to evert upon application of a longitudinal force to remove the implantable lead.

In certain embodiments the tubular cover may be formed by longitudinally or helically wrapped films. Various desired configurations may be achieved by varying film materials and characteristics (e.g., thickness and width), wrapping parameters such as wrap angles and lap width, and finished thickness of the cover. Alternatively, the tubular cover may be extruded, for example directly over a lead body or as a pre-manufactured item subsequently attached to a lead.

The tubular cover provides for atraumatic removal of the device following implantation. Atraumatic removal connotes extraction or removal of an implanted device by a means which reduces or decreases damaging shear forces to surrounding tissues associated with removal of the implanted device. A reduction or decrease is measured by comparison to removal of a similar device without the tubular cover of the invention. Without being bound to any particular theory, it is believed that atraumatic removal of implantable devices is accomplished in the present device via the tubular cover which is everted upon removal thus reducing the force required for removal of the implantable device and minimizing the trauma and tissue damage associated with removal of such devices, e.g., traditional pacing and ICD leads. This force reduction is believed due to extraction forces being converted primarily into peel force, which is localized at the distal end of the everting tubular cover and especially at the edge where the outer tube surface is being everted into an inner tube surface as the implantable device, to which the cover is attached, is being withdrawn. This differs from other extraction techniques, such as traction, where extraction forces, such as shear forces, may exist along a substantial length of the implantable device.

As demonstrated herein, use of a tubular cover in accordance with the present invention reduces the shear force needed to remove an implantable lead by at least 3-fold. See Table 1 below.

Said tubular cover can be constructed from any flexible biocompatible material. Such material can be porous, non-porous, permeable, and/or impermeable. Examples of such materials include, but are not limited to, silk, silicone, fluoropolymers such as expanded polytetrafluoroethylene (ePTFE), high density polyethylene (HDPE), and other polymers such as polyesters and polyimides. As used herein, the term "porous" describes a material that contains small or microscopic openings, or pores. Without limitation, "porous" is inclusive of materials that possess pores that are observable under microscopic examination. "Non-porous" refers to materials that are substantially free of pores. The term "permeable" describes a material through which fluids (liquid and/or gas) can penetrate or pass, particularly biological fluids. "Impermeable" describes materials that block the passage of fluids. It should be appreciated that a material may be non-porous yet still be permeable to certain substances.

Said tubular cover is constructed by methods known in the art, e.g. extrusion, and will depend on the materials used to make said tubular cover. In one embodiment, the tubular cover is constructed of materials which inhibit tissue ingrowth which may further enhance evertability. In another embodiment, said materials may be impregnated, filled, imbibed or coated with at least one chemical compound known to inhibit tissue ingrowth and/or deliver other clinical benefit, for example, chemical compounds that cause a bioactive response. Compounds that cause a bioactive response comprise anti-microbials (e.g. anti-bacterials and anti-virals), anti-inflammatories (e.g. dexamethasone and prednisone), anti-proliferatives (e.g. taxol, paclitaxel and docetaxel) and anti-coagulating agents (e.g. heparin, abciximab, eptifibatide and tirofibran). In one embodiment, said anti-inflammatory is a steroid. In another embodiment, said steroid is dexamethasone. Said tubular cover can also be impregnated, filled, imbibed or coated with electrically conductive materials, such as carbon, radio-opaque elements to foster visualization during implantation and/or extraction and/or with materials which "lubricate" the cover, thus allowing the material to slide smoothly across itself. In another embodiment, said tubular cover can be coated and/or wetted immediately before implantation by the physician and/or nurse and/or technician. In another embodiment, the invention comprises a kit comprising a tubular cover and a wetting agent for wetting said tubular cover. In another embodiment, the invention comprises a kit comprising a tubular cover, a medical device and a wetting agent for wetting said tubular cover. Said wetting agent can be any agent herein above and/or a combination of agents described herein and/or any agent that can be used to wet said tubular cover.

In another embodiment, the tubular cover can be constructed from a material which inhibits tissue (i.e. cellular) ingrowth and which is evertable upon application of a longitudinal force used to remove the implantable device, thereby reducing the force required to remove the device. Although tissue ingrowth may not be a significant problem for removing said implantable device in this embodiment, there can still be tissue attachment to said tubular cover, which can cause tissue damage when said lead is extracted.

Expanded polytetrafluoroethylene is a preferred material for the tubular cover due to its thinness, strength, biocompatibility, lubricity, ability to evert in a tubular form, and upon appropriate treatment, to become "wettable" and thus electrically transmissive. EPTFE is a porous material that is comprised of a thin, high strength, stretched, non-woven web of polytetrafluoroethylene composed substantially of nodes interconnected by fibrils. In addition, ePTFE can be engineered to have a microstructure that can modulate the degree of tissue ingrowth/incorporation and/or attachment/adhesion. In one embodiment, said tubular cover is made from ePTFE material that will not allow ingrowth/incorporation and/or attachment/adhesion. In another embodiment, said ePTFE fibrils have mean length of less that about 3.0 microns, about 1.0 microns and more preferably between about 0.05 and about 0.4 microns. In this embodiment, ePTFE will not allow tissue ingrowth/incorporation and/or attachment/adhesion. It is recognized that the above pore sizes are an average of a specific piece of material and that some larger pores in the material may allow a minor amount of cellular ingrowth/incorporation and/or attachment/adhesion. The pores sizes, shapes and quantity can also be engineered to allow penetration of conductive bodily fluids while restricting the ingrowth of tissue. In another embodiment, the ePTFE can have a mean fibril length that encourages ingrowth/incorporation and/or attachment/adhesion (typically having a mean fibril length greater than about 6.0 microns). The mean fibril length of ePTFE is estimated by examination of scanning electron photomicrographs of the surfaces of the particular film samples.

In another embodiment, said tubular cover is made from ePTFE which has been engineered to encourage ingrowth/incorporation and/or attachment/adhesion in specific sections of the tubular cover, while, in other sections, said ePTFE (or other material) will not allow for cellular ingrowth and/or cellular adhesion. In this embodiment, the microstructure of said ePTFE can be varied as a function of length along the tubular cover. For example, in some locations, at least one narrow band of material which encourages ingrowth/adhesion is placed on or along a portion or segment of the tubular cover. Said narrow band can be placed longitudinally along said medical device (either in segments or across the entire length of the medical device) or circumferentially around (in specific areas) said medical device. Said portion of the tubular cover that encourages ingrowth/incorporation and/or attachment/adhesion can help anchor the medical device in place and/or provides a constraining force that ensures eversion will occur when said medical device is extracted. In another embodiment, said bands of ePTFE that encourages ingrowth/incorporation and/or attachment/adhesion is generally located around the distal ends of tear away covers so as to provide a constraining force that ensures that tearing and eversion will occur when said medical device is extracted. In another embodiment, said bands of ePTFE that encourages cellular ingrowth/adhesion is located in any area that ensures eversion when said medical device is extracted.

It may also be desirable to modify the ePTFE used for the present invention by incorporating various additives with said ePTFE. Fillers can be incorporated in ePTFE by known methods, such as the methods taught by U.S. Pat. No. 5,879,794, to Korleski. Additives can also be imbibed into the ePTFE by known methods. Additives can also be coated on the ePTFE by known methods. Suitable additives include, for example, materials in particulate and/or fiber form and can be polymers, adhesives, elastomers, ceramics, metals, metalloids, carbon, and combinations thereof. Particularly useful additives include, for example, radiopaque materials, such as certain metals (e.g. barium alloys) and carbon. The additives can be used in combination with desired adhesive materials when incorporated with the polymer. It may also be desirable to metalize the ePTFE or at least a portion thereof. An additive may be included in the matrix of the polymer itself, or contained within the voids defined by the polymeric structure, or both. Desirable fillers may also include colorants, medicaments, anti-microbials, antivirals, antibiotics, antibacterial agents, anti-inflammatory agents, anti-proliferative agents, anti-coagulating agents, hemostatic agents, analgesics, elastomers and mixtures thereof. Compounds which lubricate an ePTFE cover, thus allowing the material to slide smoothly across itself, can be used to coat, fill, or imbibe the cover. Solid lubricants (i.e. graphite, waxes, silicone), fluid lubricants (i.e. hydrocarbon oils, silicone oils), gels (i.e. hydrogel) or any other biocompatible material known in the art may be used. In one embodiment, the whole cover incorporates at least one additive. In another embodiment, only a portion of said tubular cover incorporates said at least one additive. In this embodiment, for example, the tubular cover incorporates at least one additive (e.g. a filler that will allow for the transfer of energy (e.g. electricity) across a portion of the tubular cover) in at least one section and has at least one different additive, or no additive, in another section.

Another embodiment of the invention comprises methods of removing a medical device comprising providing an extraction force to said medical device that comprises a tubular cover that everts upon extraction. In one embodiment, said medical device comprises an implantable transmission lead. In another embodiment, said implantable transmission lead is for cardiac applications. In another embodiment, said implantable transmission lead is for neurological applications. In another embodiment, the tubular cover comprises ePTFE.

In another embodiment, said method of removing a medical device comprises separating said evertable tubular cover away from the medical device and extracting said medical device. In another embodiment, said method comprises separating the layers of said tubular cover, in a "double walled" construction, and extracting said medical device. Said separation of the tubular cover away from the medical device or from itself, in a double walled construction, reduces friction between the tubular cover and said medical device or between the tubular cover material sliding across itself and, in turn, reduces the force required to remove the medical device. In one embodiment, said method separation of the tubular cover from said medical device or from itself comprises pumping a fluid (e.g. saline), gas (e.g. air), and/or another substance (e.g. gel or other lubricating agent) that will separate said tubular cover from said medical device or from itself. In another embodiment, said medical device comprises an implantable transmission lead. In another embodiment, said implantable transmission lead is for cardiac applications. In another embodiment, said implantable transmission lead is for neurological applications.

Another embodiment of the invention comprises a method of making a medical device comprising, positioning a tubular cover over said medical device such that said cover everts upon application of a longitudinal force when removing said medical device from the body. In one embodiment, said medical device comprises an implantable transmission lead. In another embodiment, said tubular cover is positioned over said transmission lead such that said cover everts upon application of a longitudinal force when removing said lead from the body. In another embodiment, said implantable transmission lead is for cardiac applications. In another embodiment, said implantable transmission lead is for neurological applications. In another embodiment, the tubular cover comprises ePTFE. Said methods of attaching the tubular cover to the implantable transmission lead is described above.

Although the medical device exemplified for use with the tubular cover of the invention comprises an implantable transmission lead, the concept of an evertable tubular cover can be applied equally well (and is contemplated as part of the invention) to any indwelling device placed into a body of an animal, e.g. a human, for a prolonged period of time and which may be removed from said body. Examples include medical devices such as lead generators, arteriovenous (A-V) access catheters, peripherally inserted central (PICC) catheter lines, venous feeding catheters, breathing tubes, feeding tubes, implanted sensing devices, or any medical device which is prone to tissue incorporation and the need for atraumatic extraction.

The following embodiments of the present invention will now be further described by way of exemplary test methods and examples which are not intended to limit the scope of the invention in any manner.

EXAMPLES

Test Methods Utilized in the Examples

Withdrawal Force

Figure 4:
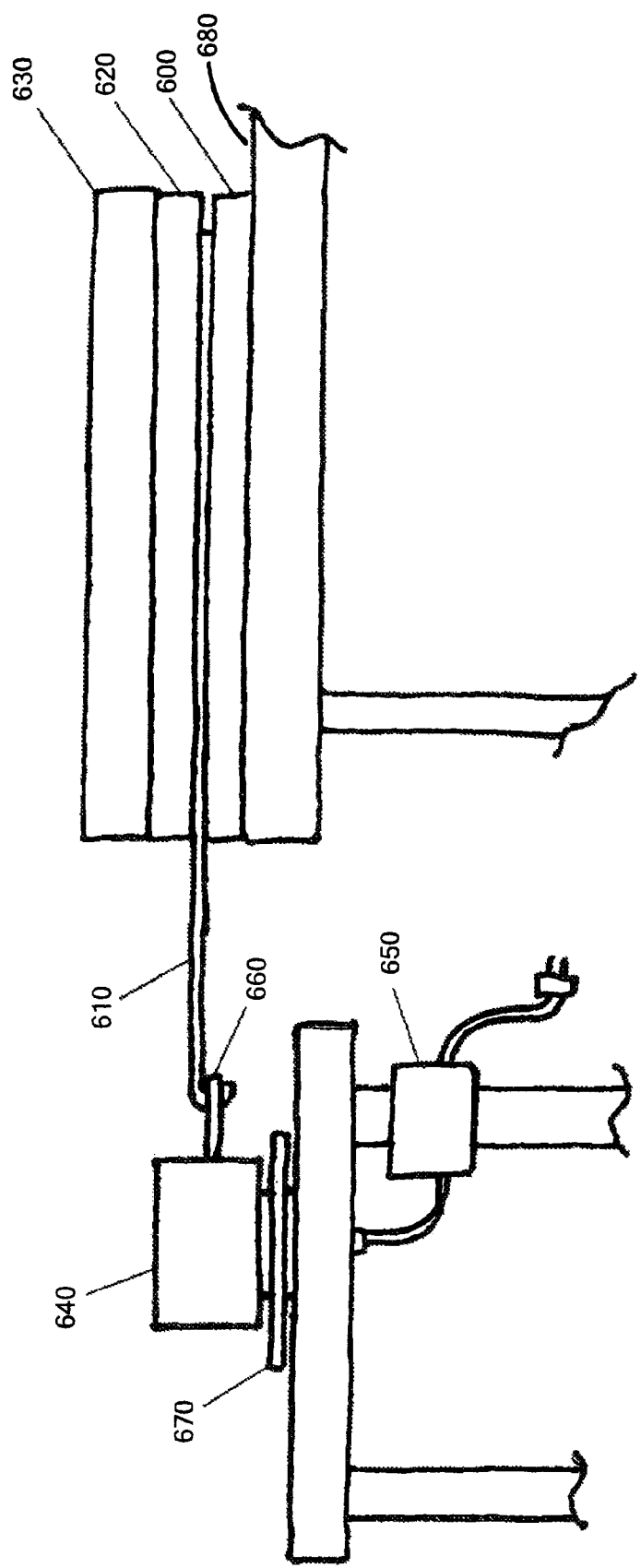
FIG. 4 is a diagram of the apparatus used to test and measure withdrawal force for a sample device.

The test apparatus is shown in FIG. 4.

Two silicone strips 600 and 620, 3.8 cm wide, 34.3 cm long, and 0.9 cm thick were cut from silicone foam rubber sheet stock (part #87485K75, McMaster Carr, Atlanta, Ga.). One strip 600 was placed on a flat surface 680.

Next, a mandrel or mandrel plus polymeric tube 610 of an example described below was placed on top of strip 600. The second strip 620 was placed on top of the mandrel or mandrel plus polymeric tube.

A 4.45 cm wide, 34.29 cm long and 2.54 cm thick rectangular steel block 630 having a mass of 3.09 kg was placed on top of the top silicone strip 620. The curved end of the mandrel 610 extended beyond the length of the strips and was attached to the hook 660 of a force gage 640 (Ametek, Accuforce III model, Ametek Corp, Paoli, Pa.). The force gage was bolted to a mounting plate 670 of a Minarik Controller 650 (Model No. WCG81596981, Minarik Corp., Glendale, Calif.).

The controller conditions were set to a traverse speed of 90 cm per minute. In this way, a longitudinal tensile force was applied to the mandrel. The bare mandrel or mandrel plus polymeric tube was pulled between the silicone strips until the mandrel was completely free of the strips. Peak force was recorded for each pull. Each test was repeated three times and the results were averaged.

Electrical Transmissivity and Release of Electrolytically Produced Gases

Figure 8:
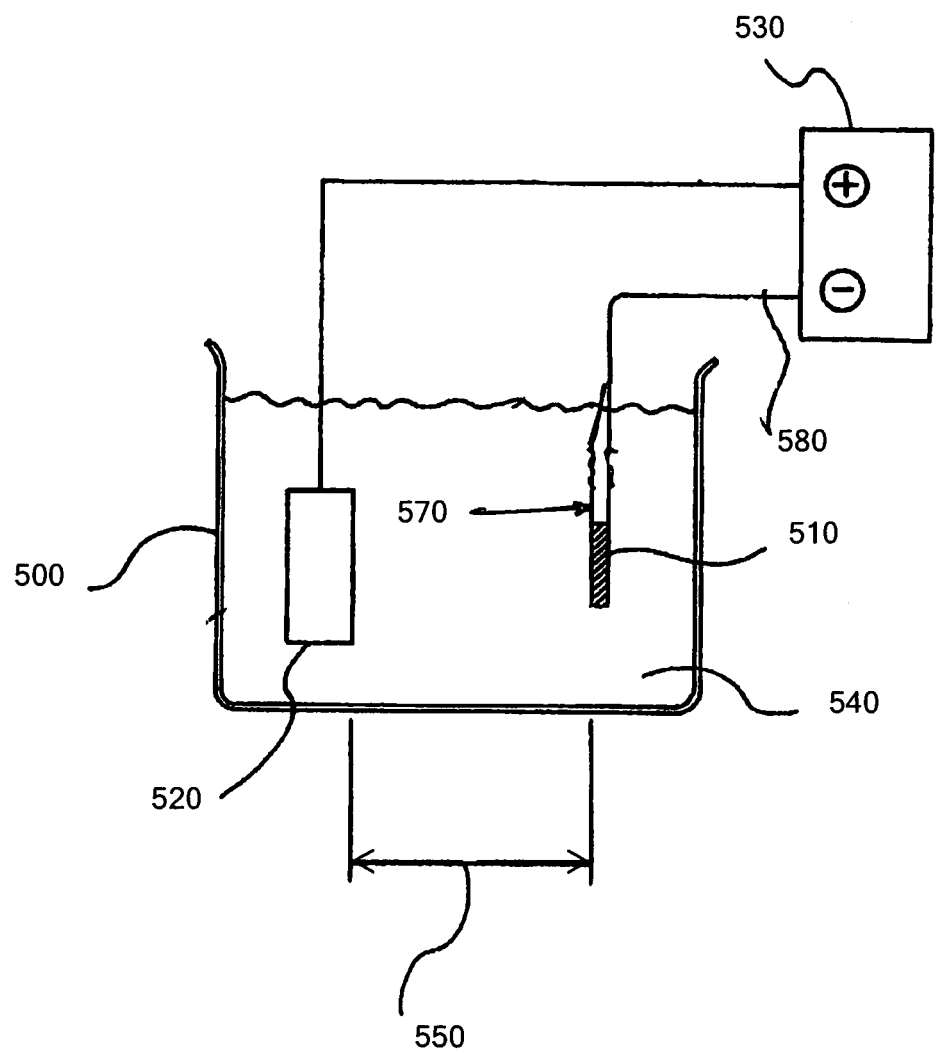
FIG. 8 is a diagram of the apparatus used to test for electrical conductance and release of electrolysis-produced gases.

The test apparatus is shown in FIG. 8.

A 500 ml glass beaker 500 was filled with 500 ml of a 0.45% sodium chloride (NaCl) solution 540. A covered coil 510 of Example 4 described below was submerged in the solution.

An indifferent electrode 520 was submerged in the solution and positioned as shown in FIG. 8, 50 mm 550 from the covered coil. The indifferent electrode 520 was connected to the positive terminal of a pulse generator 530 (Heartstart MRX, Philips Medical Systems, N.A., Bothell, Wash.). The covered coil 510 was connected to the negative terminal of the pulse generator by attaching both loose ends 570 of the coil 510 to an alligator clip 580 on a lead 580 connected to the pulse generator.

Electrical pulses of varying energy levels were applied between the covered coil and the indifferent electrode and the impedances measured. The coil cover was removed from the test apparatus and visually inspected for mechanical disruption.

Material Properties

Material thickness was measured using a digital thickness gauge with a 1.3 cm diameter foot (Model ID-C112E, Mitutoyo, Aurora, Ill.). Five measurements were made and averaged. Length and width of the material were measured using a metal ruler. Five measurements were made and averaged.

Material was weighed using a precision analytical balance (model PM400, Mettler-Toledo, Inc, Columbus, Ohio). Maximum load was measured using a tensile test machine equipped with a 10 kg load cell (Model 5564, Instron, Grove City, Pa.). The gauge length was 2.5 cm and the cross-head speed was 25 mm/minute.

Tensile test samples were 7.60 cm×2.50 cm. Longitudinal tensile test measurements were taken in the length direction of the material and transverse tensile test measurements were taken in the direction orthogonal to the length direction. The longitudinal and transverse matrix tensile strengths (MTS) were calculated using the following equation:

$$\text{Matrix Tensile Strength} = \frac{(\sigma \text{ sample}) * (\rho \text{ PTFE})}{(\rho \text{ sample})}$$

Where:
ρ PTFE=2.2 grams/cc
σ sample=(Maximum Load/Width)/Thickness
ρ sample=(Mass/Area)/Thickness Density was calculated using the formula, density=mass/volume. The average of three values was reported.

The permeability of the material was measured using a Gurley Permeability instrument, equipped with a 2.5 cm orifice area (Model 4110, Teledyne Gurley, Troy Mich.). Values were recorded as the time in seconds for 300 cc of air to flow through a 6.45 cm² sample. The average of three sample measurements was used.

The maximum pore size of three samples of material was measured as the isopropyl alcohol bubble point using a pressure regulator bubble point tester (Model LC-APOK, Salt Lake City, Utah). The three values were averaged and reported.

Ethanol bubble point (EBP) is the minimum pressure required to force air through an ethanol-saturated material (such as ePTFE). Raising the pressure slightly should produce steady streams of bubbles at many sites. Thus, the measurements are not biased by artifacts such as puncture holes in the material. Ethanol bubble point is inversely related to pore size; lower values of EBP indicate larger pores. It is believed that EBP can be assumed to be independent of the length of the path that the air travels through the article. In other words, it is believed that EBP provides a characterization of pore size that is not unacceptably dependent on the dimensions of the tested article. Note the data below is based on an isopropyl (not ethanol) bubble point test.

Comparative Example 1

Bare Mandrel

Figure 5:
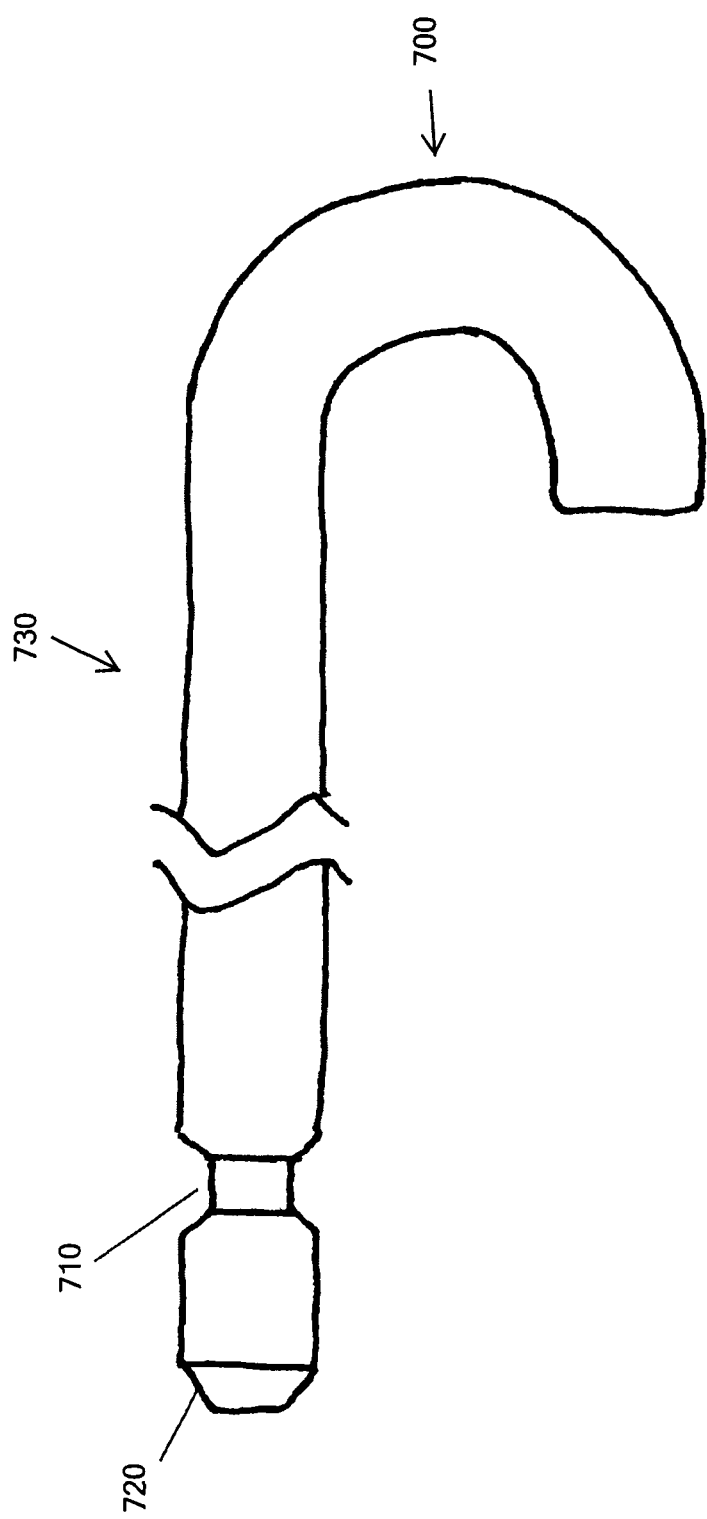
FIG. 5 is a close-up of the mandrel of the apparatus of FIG. 4.

Referring to FIG. 5, a straight, solid stainless steel mandrel 730 measuring 35.60 cm long and 0.25 cm diameter (available from New England Precision Grinding, Holliston, Mass.) was obtained. A 0.25 mm deep and 1.15 mm wide groove 710 was cut around the circumference of the mandrel 730, 4.73 mm from one end. A chamfer 720 was formed at the grooved end of the mandrel. 15 mm of the other end of the mandrel was bent into a hook shape 700 as shown in FIG. 5.

The force to withdraw the mandrel from between the two silicone strips was measured as described above. The average of the peak forces was 4.00 kg, as seen in Table 1.

Comparative Example 2

Single Walled Tube Attached at Curved End of Mandrel

Expanded polytetrafluoroethylene (ePTFE) material was obtained with the following properties: Thickness=0.0025 microns, Width=6.5 cm, Length=25.4 cm, Mass/Area=2.5 g/m2, Longitudinal MTS=558.5 MPa, Transverse MTS=29.6 MPa, Gurley number=2 sec/6.45 cm2/100 cc, and IPA Bubble Point=0.23 MPa.

A straight, solid stainless steel mandrel measuring 35.6 cm long and 0.25 cm diameter (available from New England Precision Grinding, Holliston, Mass.) was obtained. Six and a half layers of the material were wrapped about the circumference of the mandrel such that the length direction of the material was oriented in the longitudinal direction of the mandrel. Consequently, a single longitudinally-oriented seam resulted. In this way, the higher strength direction of the ePTFE material was oriented along the longitudinal axis of the mandrel. A soldering iron (Model Weller WESD51, Cooper Industries, Houston, Tex.), set at 343.3° C. was passed along the full length of the seam.

The mandrel plus ePTFE was placed in a forced air oven (Grieve Model NT1000, single phase, Grieve Corp, Round Lake, Ill.) set to 370° C. for 7 minutes then removed from the oven and allowed to cool. An ePTFE tube resulted. The tube was removed from the mandrel.

A curved end mandrel, as described in Comparative Example 1 was obtained. The ePTFE tube was slid over the grooved end of the curved end mandrel. A drop of Loctite 495 adhesive (Henkel Australia PTY. LTD., 1 Clyde St., Sliverwater NSW229, Australia) was applied to the edge of the tube nearer the curved end. A 1.0 cm long piece of 0.32 cm diameter shrink tube (Part no. HS-101, Insultab, 45 Industrial Parkway, Woburn, Mass.) was slid over the mandrel to cover the tube edge to which the adhesive had been applied. The shrink tubing was heated at 211.6° C. for 10 seconds in order to assist the bonding of the tube to the mandrel. This was done using a thermal box (Balloon Development Station #210A, Beahn Designs, Los Gatos, Calif.), with air output set at 25 standard cubic feet per hour (SCFH). The adhesive was allowed to cure under ambient conditions for 0.5 hours.

The force to withdraw the mandrel plus the ePTFE tube from between the two silicone strips was measured as described above. The average of the peak forces was 3.72 kg, as seen in Table 1.

Example 3

Single Walled Tube, Everting as Removed

An ePTFE tube was constructed and placed over a curved ended mandrel as described in Comparative Example 2.

Figure 6A:
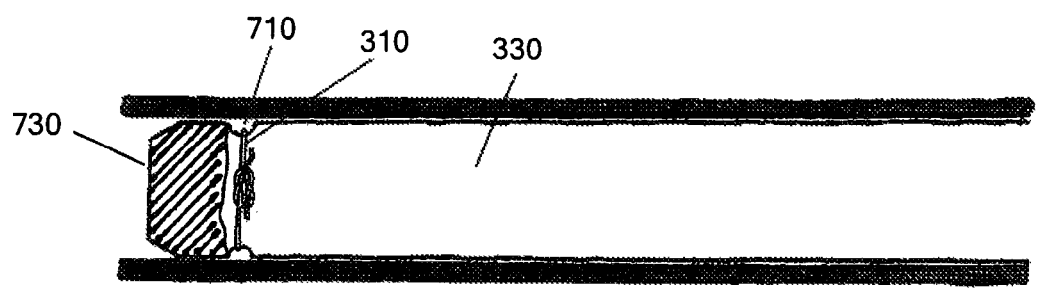
FIGS. 6A and 6B shows attachment of a tubular cover of the present invention, which everts upon removal, over a mandrel for measurement of withdrawal force as described in Example 3.

Referring to FIG. 6A, the ePTFE tube 330 was attached to the mandrel 730 at the groove 710 using one loop of suture 310 (CV5, W.L. Gore and Assoc., Flagstaff, Ariz.) and secured with a square knot. The knot was pressed into the groove to minimize profile.

The mandrel plus ePTFE tube were then tested as described above.

Figure 6B:
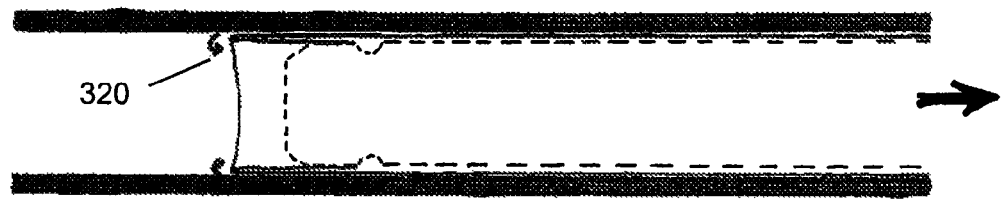

In this case, as longitudinal force (shown buy an arrow in FIG. 6B) was applied, the tube everted, as shown by curved arrows 320 as the mandrel was withdrawn. The average of the peak forces was 1.23 kg, as seen in Table 1.

Example 4

Double Walled Tube, Everting as Removed

An ePTFE tube was constructed as described in Comparative Example 2, except that it was made twice as long (50.8 cm).

Figure 7A:
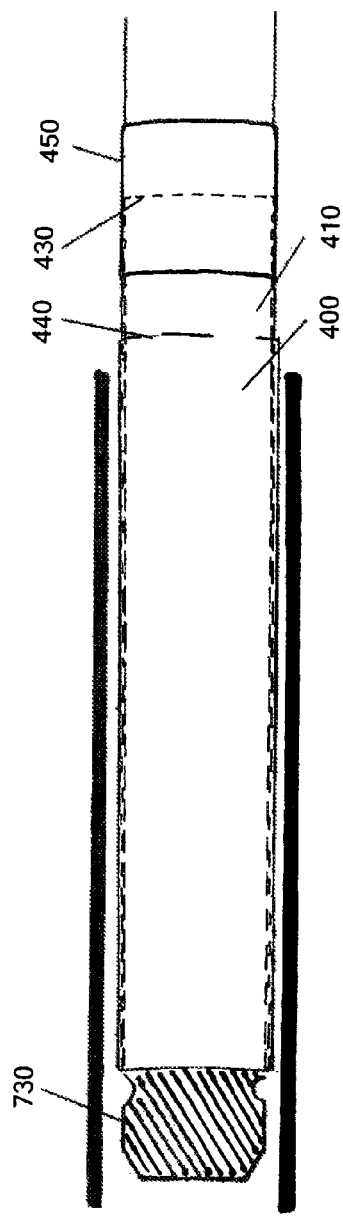
FIG. 7A through 7C are diagrams showing attachment of a double walled tubular cover attached to a mandrel for measurement of withdrawal force as described in Example 4.
Figure 7B:
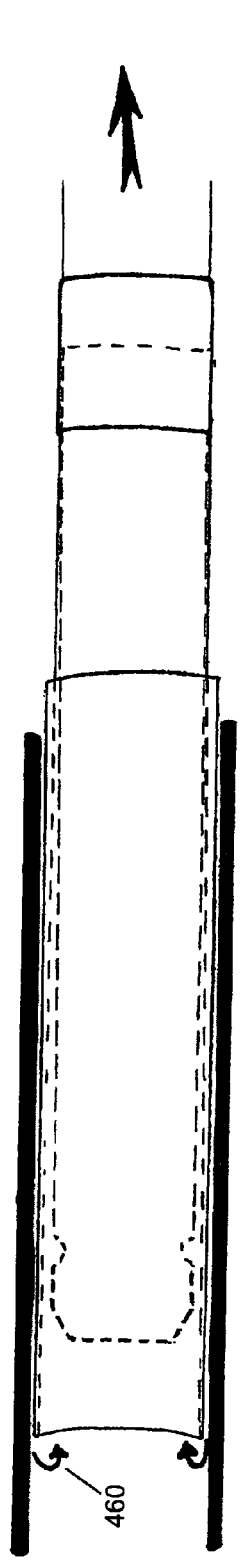
Figure 7C:
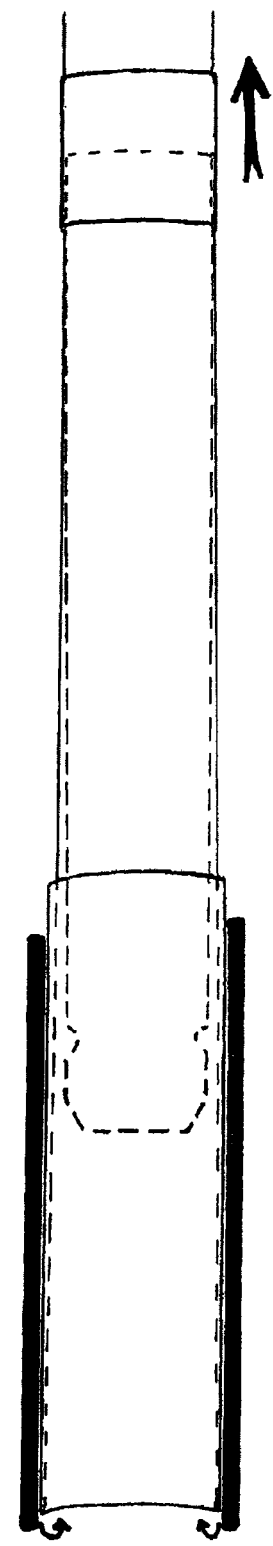

Referring to FIG. 7A, a curved end mandrel 730, as described in Comparative Example 1, was obtained. One half of the tube was placed over a mandrel and attached at the curved end using an adhesive and shrink tube, as described in Comparative Example 2. The other half of the tube was then folded back over the first half of the tube, toward the curved end of the mandrel 730, creating two layers 400 and 410 of tube material over the length of the mandrel 730 as shown in FIGS. 7A through 7C. Also shown in FIGS. 7A through 7C is the shrink tube 450, first tube end 430 and second tube end 440.

The mandrel was then withdrawn as indicated by the straight arrow in FIGS. 7B and 7C. The tube everted, as shown by curved arrows 460 as the mandrel was withdrawn. The force to withdraw the mandrel plus the ePTFE tube from between the two silicone strips was measured as described above. The average of the peak forces was 1.20 kg, as seen in Table 1.

Example 5

Single Walled Tube HDPE Tube Everts as Removed

High density polyethylene (HDPE) material was obtained from a can liner (part #HR171806C, Waverly Plastics, Waverly, Iowa). The HDPE film material was 6.5 cm wide, 25.4 cm long and 0.006 mm thick. A tube was created by longitudinally wrapping the HDPE material film on a straight, solid stainless steel mandrel as described in Comparative Example 2.

The only difference from that example was that bonding of the seam was achieved through the use of silicone adhesive (Adhesive Silicone Type A, Part no. MED1137, NuSil Technology, Carpenteria, Calif.). The adhesive was allowed to cure under ambient conditions overnight.

The HDPE tube was removed from the mandrel. The HDPE tube was mounted on a curved end mandrel and attached to the mandrel as described in Example 3. The force to withdraw the mandrel plus the HDPE tube from between the two silicone strips was measured as described above. The HDPE tube everted upon withdrawal. The average of the peak forces was 1.12 kg, as seen in Table 1.

TABLE 1

Withdrawal forces

| Comparative Example 1 | Comparative Example 2 | Example 3 | Example 4 | Example 5 |
|---|---|---|---|---|
| 4.00 kg | 3.72 kg | 1.23 kg | 1.20 kg | 1.12 kg |

Example 6

Electrical Transmissivity and Release of Electrolytically Produced Gases

A silver plated copper rod, 2.4 mm in diameter and 20.3 cm in length was obtained (Phelps Dodge Industries, Co., Phoenix, Ariz.). A coil was produced by wrapping the center portion of the rod with a 0.15 mm diameter wire having a 25% silver core and a nickel-cobalt-chromium-molybdenum outer layer. (MP 35N DFT, 25% Ag, Fort Wayne Metals, Fort Wayne, Ind.). The coil was wrapped without gaps between the wires. The finished coil measured 6.3 mm in length. About 3.0 cm of wire was left unwrapped and loose on each end of the coil.

Expanded polytetrafluoroethylene (ePTFE) material with the properties given in Comparative Example 2 was obtained. The material was wrapped around the coil as described in Comparative Example 2. The material was seam sealed as described in Comparative Example 2. The rod and coil plus ePTFE assembly was placed in a forced air oven (Grieve Model NT1000, single phase, Grieve Corp, Round Lake, Ill.) set to 370° C. for 10 minutes then removed from the oven and allowed to cool.

One end of the silver plated copper rod was clamped into a vice and the other was gripped with a set of vice grips and pulled in the length direction. This reduced the diameter of the rod underneath the coil allowing it to slip off the rod.

Referring to FIG. 8, the covered coil 510 was then chemically treated as follows. It was soaked in isopropyl alcohol (IPA) at ambient temperature (about 21° C.) for 15 minutes. Then it was immediately transferred to a solution of 2.0% polyvinyl alcohol (PVA) and de-ionized water and allowed to soak at ambient temperature for 70 minutes. The covered coil was rinsed for 20 minutes in de-ionized water at ambient temperature and then soaked for 50 minutes in a solution of 2% gluteraldehyde, 1% hydrochloric acid (HCL) and de-ionized water, at ambient temperature. The covered coil was rinsed in de-ionized water at ambient temperature for 2 hours and then allowed to dry in ambient air. It was then placed into the test apparatus as shown in FIG. 8 and allowed to soak for 1 minute. The loose wires at each end 570 were attached to the pulse generator lead 580 via a lead 580.

The pulse generator was set to deliver 30 J electrical pulses and a pulse was delivered between the covered coil and the indifferent electrode. This was repeated 3 times at 30-40 second intervals. The pulse generator was then set to the following conditions: 50 J and 50 seconds between pulses; 70 J and 18 seconds between pulses; 100 J and 11 seconds between pulses; 150 J and 15 seconds between pulses; 150 J and 18 seconds between pulses.

The electrical continuity of the covered coil in the test apparatus was retained for the duration of the test as evidenced by the visual detection of gas microbubble electrolysis emitted from the length of the covered coil during each pulse and measured impedances for each pulse remaining in a narrow range of between 26.2-27.7 ohms.

The covered coil was removed from the test apparatus, dried and inspected using a 30× stereo microscope. No mechanical disruption (tears or holes) were noted in the cover of the coil. No mechanical damage to the coil was observed.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. An implantable tubular medical device comprising a tubular cover, the tubular cover comprising at least one axial location including means of permitting circumferential tearing of the tubular cover, the tubular cover configured to tear and evert upon application of a longitudinal force to the medical device following implantation when the medial device is extracted.

2. The medical device of claim 1, wherein the medical device is chronically implanted in an animal.

3. The medical device of claim 2, wherein the medical device is prone to tissue incorporation.

4. The medical device of claim 1, wherein the medical device is selected from the group consisting of lead generators, arteriovenous (A-V) access catheters, peripherally inserted central (PICC) catheter lines, venous feeding catheters, breathing tubes, and implanted sensing devices.

5. The device of claim 4, wherein the tubular cover allows for a transfer of energy.

6. The device of claim 5, wherein the energy is electrical energy.

7. The device of claim 1, wherein the tubular cover comprises ePTFE.

8. The device of claim 7, wherein the ePTFE comprises at least one additive.

9. The device of claim 8, wherein the additive is a lubricating agent.

10. The device of claim 8, wherein only a portion of the tubular cover comprises an additive.

11. The device of claim 8, wherein the additive elicits a bioactive response.

12. The device of claim 11, wherein the bioactive response is selected from the group consisting of an anti-inflammatory, anti-microbial, and an anti-proliferative response.

13. The device of claim 7, wherein the tubular cover modulates a degree of tissue ingrowth and/or adhesion.

14. The device of claim 1, wherein the tubular cover resists tissue ingrowth and/or adhesion.

15. The device of claim 1, wherein the medical device comprises an implantable lead having a length, a distal end, a proximal end, an outer surface and a longitudinal axis, wherein the tubular cover is positioned over a substantial portion of the outer surface of the implantable lead, the tubular cover being physically coupled to the implantable lead at a location distal to each of the at least one axial location including means for permitting the circumferential tearing of the tubular cover, wherein the tubular cover is configured to tear and evert upon application of a longitudinal force effective to cause the implantable lead to move in a proximal direction during removal of the implantable lead from anatomy, wherein upon eversion the tubular cover folds into itself.

16. The device of claim 15, wherein the implantable lead is a therapeutic or diagnostic lead.

17. The device of claim 15, wherein the implantable lead is a transmission lead.

18. The device of claim 17, wherein the transmission lead is for cardiac applications.

19. The device of claim 17, wherein the transmission lead is for neurological applications.

20. The device of claim 15, wherein the tubular cover comprises ePTFE.

21. The device of claim 20, wherein the ePTFE comprises at least one additive.

22. The device of claim 21, wherein the additive is a lubricating agent.

23. The device of claim 21, wherein the additive helps conduct electrical energy across said tubular cover.

24. The device of claim 21, wherein the additive elicits a bioactive response.

25. The device of claim 24, wherein the bioactive response is selected from the group consisting of an anti-inflammatory, an anti-microbial and an anti-proliferative response.

26. The device of claim 20, wherein the tubular cover modulates tissue ingrowth and/or adhesion.

27. The device of claim 15, wherein the tubular cover resists tissue ingrowth and/or adhesion.

28. The device of claim 15, wherein the tubular cover allows for transfer of energy.

29. The device of claim 28, wherein the energy is electrical energy.

30. The device of claim 29, wherein the cover is electrically transmissive upon wetting.

31. The device of claim 29, wherein the tubular cover allows for transfer of gases generated by electrolysis.

32. The device of claim 15, wherein the tubular cover is attached to the implantable lead at least at the distal end of the lead.

* * * * *